United States Patent
Dominijanni et al.

(10) Patent No.: US 10,623,846 B2
(45) Date of Patent: Apr. 14, 2020

(54) EARPIECES EMPLOYING VISCOELASTIC MATERIALS

(71) Applicant: Bose Corporation, Framingham, MA (US)

(72) Inventors: Andrew D. Dominijanni, Newton, MA (US); Shawn J. Prevoir, Northborough, MA (US); Lei Cheng, Wellesley, MA (US); Ryan C. Struzik, Hopkinton, MA (US); Eric M. Wallace, Andover, MA (US); Agota F. Fehervari, Lexington, MA (US); Zarif Farhana Mohd Aris, Arlington, MA (US)

(73) Assignee: Bose Corporation, Framingham, MA (US)

( * ) Notice: Subject to any disclaimer, the term of this patent is extended or adjusted under 35 U.S.C. 154(b) by 389 days.

(21) Appl. No.: 15/370,516

(22) Filed: Dec. 6, 2016

(65) Prior Publication Data

US 2018/0160216 A1    Jun. 7, 2018

(51) Int. Cl.
| | |
|---|---|
| *H04R 1/10* | (2006.01) |
| *A61F 11/06* | (2006.01) |
| *C08F 32/08* | (2006.01) |
| *C08G 61/08* | (2006.01) |
| *C08L 65/00* | (2006.01) |

(52) U.S. Cl.
CPC ............ *H04R 1/1066* (2013.01); *A61F 11/06* (2013.01); *C08F 32/08* (2013.01); *H04R 1/105* (2013.01); *C08G 61/08* (2013.01); *C08G 2261/3324* (2013.01); *C08G 2261/60* (2013.01);
(Continued)

(58) Field of Classification Search
CPC ............ A61B 5/02427; A61B 5/024; B32B 17/10761; B32B 17/10; B32B 25/20; E04B 1/84; H04R 1/105; H04R 1/1058; H04R 1/1066; H04R 1/1016; H04R 25/658; H04R 2201/029; H04R 23/008; A61F 11/06; C08F 32/08; C08F 290/12; C08G 61/08; C08G 2261/3324; C08G 2261/60; C08G 65/333; C08G 59/32; C08G 18/48; C08L 65/00; C08L 71/12; C08L 67/04; B01L 3/00; C09J 153/00; C09J 3/215; C09J 7/10; A61K 8/81; C08J 3/22; C08J 3/215

USPC ....... 381/328, 370, 380, 381, 382, 150, 371; 428/299.1, 403, 519, 373, 156, 317.3; 524/302, 412, 447, 484, 853, 55, 600, 524/528; 525/190, 191, 232, 387, 240; 600/559, 347, 437; 602/54; 181/129; 257/98, 416; 623/1.11; 8/160; 34/282; 132/73; 264/211.24; 267/140.4; 367/73; 424/61, 70, 13, 423, 600; 442/149, 327, 442/188; 473/342; 526/279, 308, 348.5

See application file for complete search history.

(56) References Cited

U.S. PATENT DOCUMENTS 4,429,068 A *  1/1984  Nakahira ............ A43B 13/181
                                                           152/310
4,623,586 A *  11/1986  Umeya .................. B29C 70/62
                                                           252/62

(Continued)

OTHER PUBLICATIONS

International Search Report and Written Opinion; PCT/US2017/064219; dated Feb. 20, 2018; 13 pages.

*Primary Examiner* — Gerald Gauthier
(74) *Attorney, Agent, or Firm* — Fish & Richardson P.C.

(57) ABSTRACT

The disclosure is related to compositions including viscoelastic materials. The compositions are suitable for use in earpieces such as in-ear earpieces.

17 Claims, 2 Drawing Sheets

(52) U.S. Cl.
CPC ............ *C08L 65/00* (2013.01); *H04R 1/1016* (2013.01); *H04R 2201/029* (2013.01)

(56) References Cited

U.S. PATENT DOCUMENTS

| | | | | |
|---|---|---|---|---|
| 5,227,424 A * | 7/1993 | Tokieda | ................ | B60C 1/0016 524/484 |
| 5,468,819 A * | 11/1995 | Goodall | ............... | C08F 232/08 526/171 |
| 5,912,313 A * | 6/1999 | McIntosh, III | ......... | C08F 32/08 526/255 |
| 6,451,945 B1 * | 9/2002 | Jayaraman | ............ | G03F 7/0045 526/281 |
| 6,639,021 B2 * | 10/2003 | Oshima | ................. | C08G 61/08 428/428 |
| 6,812,170 B1 * | 11/2004 | Himmelsbach | ..... | A61F 13/0256 428/343 |
| 6,856,690 B1 * | 2/2005 | Skulley | ............... | H04R 1/1008 381/367 |
| 6,863,989 B1 * | 3/2005 | Dyatlov | ................ | C09J 123/10 428/500 |
| 6,890,847 B1 * | 5/2005 | Farrar | ................. | C08L 65/00 438/623 |
| 7,326,753 B2 * | 2/2008 | Weller | ................... | C08L 23/06 525/284 |
| 7,378,456 B2 * | 5/2008 | Elce | ...................... | C08F 220/40 252/182.24 |
| 7,863,382 B2 * | 1/2011 | Ishii | ....................... | C08L 67/04 525/190 |
| 8,075,956 B2 * | 12/2011 | Geddes | .................. | B05D 7/02 427/402 |
| 8,123,971 B2 * | 2/2012 | Bose | ......................... | C08J 5/10 252/62.54 |
| 8,470,944 B2 * | 6/2013 | Knapp | .................. | B01D 61/362 210/500.23 |
| 9,068,346 B1 | 6/2015 | Lu | ........................ | G10K 11/162 |
| 9,090,730 B1 | 7/2015 | Mazumdar | .............. | C08K 3/36 |
| 9,109,073 B1 | 8/2015 | Ma | ......................... | C08F 2/38 |
| 9,835,416 B1 | 12/2017 | Roland | .................... | F41H 5/04 |
| 10,144,825 B2 | 12/2018 | Topolkaraev | .......... | C08L 23/0807 |
| 2003/0044038 A1* | 3/2003 | Shirata | .................. | H04R 1/105 381/381 |
| 2003/0125469 A1* | 7/2003 | Golze | ..................... | C08L 23/06 525/232 |
| 2004/0122174 A1* | 6/2004 | Mather | ............. | C08G 18/3893 525/191 |
| 2004/0122184 A1* | 6/2004 | Mather | ............. | C08G 18/3893 525/387 |
| 2005/0010275 A1* | 1/2005 | Sahatjian | ................. | A61F 2/88 623/1.11 |
| 2005/0019292 A1* | 1/2005 | Acher | ................... | A61K 8/25 424/70.13 |
| 2005/0113540 A1* | 5/2005 | Weaver | ................ | C08F 210/02 526/308 |
| 2005/0216074 A1* | 9/2005 | Sahatjian | ................. | A61F 2/88 623/1.11 |
| 2006/0037624 A1* | 2/2006 | Ilekti | ..................... | A45D 29/001 132/73 |
| 2006/0104158 A1* | 5/2006 | Walls | ...................... | G01V 1/30 367/73 |
| 2006/0204537 A1* | 9/2006 | Ratner | ................. | A61K 9/0024 424/423 |
| 2007/0093589 A1* | 4/2007 | Proctor | ................. | C08K 3/346 524/447 |
| 2007/0189570 A1* | 8/2007 | Matsuo | ................. | H04R 1/1016 381/382 |
| 2007/0276242 A1* | 11/2007 | Konofagou | .............. | A61B 8/08 600/437 |
| 2008/0102984 A1* | 5/2008 | Chiang | ................. | A63B 53/04 473/342 |
| 2008/0181441 A1* | 7/2008 | Smith | .................. | H04R 1/1016 381/328 |
| 2008/0217709 A1* | 9/2008 | Minervini | ............. | B81B 7/0061 257/416 |
| 2008/0263890 A1* | 10/2008 | Picard | .................... | B30B 15/34 34/282 |
| 2008/0308967 A1* | 12/2008 | Kulikov | ................ | C08F 255/00 264/211.24 |
| 2009/0134098 A1* | 5/2009 | Eng | .......................... | A61K 8/19 424/600 |
| 2010/0040246 A1* | 2/2010 | Windischberger | ........ | H04R 7/10 381/150 |
| 2010/0137775 A1* | 6/2010 | Hu | ...................... | A61M 1/0088 602/54 |
| 2010/0146715 A1* | 6/2010 | Ellis | ........................ | A61K 8/25 8/160 |
| 2010/0178262 A1* | 7/2010 | Kergosien | ................ | A61K 8/361 424/61 |
| 2010/0236564 A1* | 9/2010 | Ilekti | .................... | A45D 29/001 132/73 |
| 2010/0286329 A1* | 11/2010 | Fukushi | .................. | C08F 14/16 524/544 |
| 2010/0322454 A1* | 12/2010 | Ambrose | ............. | H04R 1/1016 381/380 |
| 2011/0092640 A1* | 4/2011 | Tzou | .................... | C08G 59/4261 524/600 |
| 2011/0217547 A1* | 9/2011 | Mather | ................. | B29C 61/003 428/339 |
| 2011/0228963 A1* | 9/2011 | Goldstein | ............ | H04R 1/1016 381/380 |
| 2011/0294955 A1* | 12/2011 | Akiba | ................... | C08L 67/025 525/173 |
| 2012/0028047 A1* | 2/2012 | Imai | .......................... | C08J 5/04 428/403 |
| 2012/0058329 A1* | 3/2012 | Sakurai | ................. | C08F 287/00 428/317.3 |
| 2012/0059105 A1* | 3/2012 | Kerstetter, III | ......... | C08L 23/10 524/412 |
| 2012/0156456 A1* | 6/2012 | Niimi | ........................ | B32B 7/12 428/214 |
| 2012/0220728 A1* | 8/2012 | Uekusa | ................. | C08F 210/00 525/240 |
| 2012/0302671 A1* | 11/2012 | Reid | ........................ | C08K 3/34 524/55 |
| 2013/0087404 A1* | 4/2013 | Peskar | ................. | G10K 11/168 181/129 |
| 2013/0202873 A1* | 8/2013 | Mizuki | .................. | C08G 59/38 428/299.1 |
| 2013/0216086 A1* | 8/2013 | Kirkpatrick | .......... | H04R 1/1058 381/380 |
| 2013/0274628 A1* | 10/2013 | Fausti | .................... | A61B 5/123 600/559 |
| 2013/0343594 A1* | 12/2013 | Howes | ................. | H04R 1/1016 381/380 |
| 2014/0099505 A1* | 4/2014 | Thunga | .................... | D01F 9/17 428/373 |
| 2014/0170919 A1* | 6/2014 | Manipatruni | ............ | D01D 5/00 442/188 |
| 2014/0349075 A1* | 11/2014 | Hendriks | ............ | B29C 37/0053 428/156 |
| 2014/0350186 A1* | 11/2014 | Hatae | .................... | C08F 265/06 525/187 |
| 2015/0087782 A1* | 3/2015 | Hoshino | ................ | B32B 27/26 524/853 |
| 2015/0146909 A1* | 5/2015 | Kirkpatrick | .......... | H04R 25/652 381/380 |
| 2015/0147545 A1* | 5/2015 | Roland | ................. | B32B 15/06 428/217 |
| 2015/0195638 A1* | 7/2015 | Tseng | .................. | H04R 1/1058 381/380 |
| 2015/0307701 A1* | 10/2015 | Croisier | ................ | C08L 89/00 524/528 |
| 2015/0368412 A1* | 12/2015 | Cermelli | .................. | C08L 23/06 526/348.5 |
| 2015/0372205 A1* | 12/2015 | Kimura | .................. | C08L 23/02 257/98 |
| 2015/0382094 A1* | 12/2015 | Grinker | ................. | H04R 1/1016 381/380 |

(56) References Cited

U.S. PATENT DOCUMENTS

| | | | |
|---|---|---|---|
| 2016/0031190 A1* | 2/2016 | Greiveldinger | B60C 1/0008 428/519 |
| 2016/0146282 A1* | 5/2016 | Collard | F16F 3/12 267/140.4 |
| 2016/0173971 A1* | 6/2016 | Lott | H04R 1/1066 381/380 |
| 2016/0200882 A1* | 7/2016 | Bhat | F41H 5/0471 442/327 |
| 2016/0241946 A1* | 8/2016 | Monahan | H04R 1/1016 |
| 2016/0287108 A1* | 10/2016 | Wei | A61B 5/02427 |
| 2016/0297967 A1* | 10/2016 | Jung | H05K 1/0353 |
| 2017/0081482 A1* | 3/2017 | Hanan | C08J 3/22 |
| 2017/0094384 A1* | 3/2017 | Trainer | H04R 1/105 |
| 2017/0094386 A1* | 3/2017 | Trainer | H04R 1/1016 |
| 2017/0099552 A1* | 4/2017 | Moulton | H04R 1/1058 |
| 2017/0121451 A1* | 5/2017 | Hayashi | C08J 5/042 |
| 2017/0134865 A1* | 5/2017 | Goldstein | B29C 35/0805 |
| 2017/0195773 A1* | 7/2017 | Morris | H04R 1/1058 |
| 2017/0216840 A1* | 8/2017 | Branch | B01L 3/502715 |
| 2017/0253010 A1* | 9/2017 | Lu | G02B 27/0149 |
| 2017/0311069 A1* | 10/2017 | Prevoir | B29C 35/0805 |
| 2018/0064626 A1* | 3/2018 | Cass | A61K 8/25 |
| 2018/0071197 A1* | 3/2018 | Pope | A61Q 9/04 |
| 2018/0103310 A1* | 4/2018 | Hornstein | H04R 1/1016 |
| 2018/0109861 A1* | 4/2018 | Prevoir | C08K 5/01 |
| 2018/0126706 A1* | 5/2018 | Erdogan-Haug | B32B 7/00 |
| 2018/0134842 A1* | 5/2018 | Nagai | C08K 3/16 |
| 2018/0160216 A1* | 6/2018 | Dominijanni | H04R 1/1066 |
| 2018/0230337 A1* | 8/2018 | Okamoto | B32B 7/12 |
| 2018/0346637 A1* | 12/2018 | Colson | C08G 18/4854 |
| 2018/0346678 A1* | 12/2018 | Prevoir | A61F 11/08 |
| 2018/0358494 A1* | 12/2018 | Pilat | H01L 31/048 |
| 2018/0376236 A1* | 12/2018 | Prevoir | H04R 1/1066 |
| 2019/0002617 A1* | 1/2019 | Kotani | C08F 290/126 |
| 2019/0085111 A1* | 3/2019 | Ohashi | C08F 18/14 |
| 2019/0085222 A1* | 3/2019 | Tse | C09J 153/00 |
| 2019/0135990 A1* | 5/2019 | Michels | C08J 3/215 |
| 2019/0144661 A1* | 5/2019 | Oda | C08K 3/00 |
| 2019/0284358 A1* | 9/2019 | Prevoir | C08J 7/14 |

* cited by examiner

EARPIECES EMPLOYING VISCOELASTIC MATERIALS

TECHNICAL FIELD

This disclosure generally relates to compositions including viscoelastic materials that are useful for earpieces for use with electronic devices.

BACKGROUND

Earpieces can be e.g., part of earphones and other devices placed within human ears for delivering audible sounds.

SUMMARY

In one aspect, described herein are examples of earpieces having a tip, retaining legs, a body, a channel, or a combination thereof made from a composition including one or more elastomers, wherein the composition has a low frequency modulus metric ($M_{lf}$) of about 0.5 to about 1, a high frequency modulus metric ($M_{hf}$) of about 0.5 to about 1, and a glass transition temperature ($T_g$) of about −25° C. to about 30° C. At least one of the one or more elastomers may be polynorbornene, polyurethane, styrenic-based thermoplastic elastomer, butyl rubber, acrylic, thermoplastic vulcanizates, nitrile rubber, etc. At least one of the one or more elastomers may be polynorbornene. The polynorbornene may have a density of about 0.8 to about 1.2 kg/dm$^3$, a hardness of about 10 to about 20 Shore A, and a tensile strength of about 2 to about 8 MPa. The composition may include polynorbornene, anti-oxidant, UV stabilizer, curatives, inhibitors, plasticizers, fillers, etc. The $T_g$ may be about 5° C. to about 30° C. The $T_g$ may be about 20° C. to about 30° C. The $T_g$ may be about 5° C. to about 25° C. The $M_{hf}$ may be about 0.7 to about 1. The $M_{lf}$ may be about 0.7 to about 1. The product of $M_{hf}$ and $M_{lf}$ may be about 0.5 to about 1.

In one aspect, provided herein are examples of earpieces having a tip, retaining legs, a body, a channel, or a combination thereof made from a composition including polynorbornene, wherein the composition has a $M_{lf}$ of about 0.7 to about 1, a $M_{hf}$ of about 0.7 to about 1, and a $T_g$ at about 10° C. to about 30° C.

In one aspect, provided herein are examples of earpieces having a tip, retaining legs, a body, a channel, or a combination thereof made from a composition including one or more elastomers, wherein the composition has a storage modulus of about 0.5 to about 50 MPa at about 25° C. and about 1 Hz, a glassy modulus of greater than about 400 MPa, and a $T_g$ at about −25° C. to about 30° C.

At least one of the one or more elastomers may be polynorbornene and the polynorbornene may have a density of about 0.8 to about 1.2 kg/dm$^3$, a hardness of about 10 to about 20 Shore A, and a tensile strength of about 2 to about 8 MPa. The composition may include polynorbornene, anti-oxidant, UV stabilizer, curatives, inhibitors, plasticizers, fillers, etc. The $T_g$ may be about 5° C. to about 30° C. The $T_g$ may be about 20° C. to about 30° C. The $T_g$ may be about 5° C. to about 25° C.

Any two or more of the features described in this specification, including in this summary section, can be combined to form implementations not specifically described herein. The details of one or more implementations are set forth in the accompanying drawings and the description below. Other features and advantages will be apparent from the description and drawings, and from the claims.

DETAILED DESCRIPTION

Figure 1:
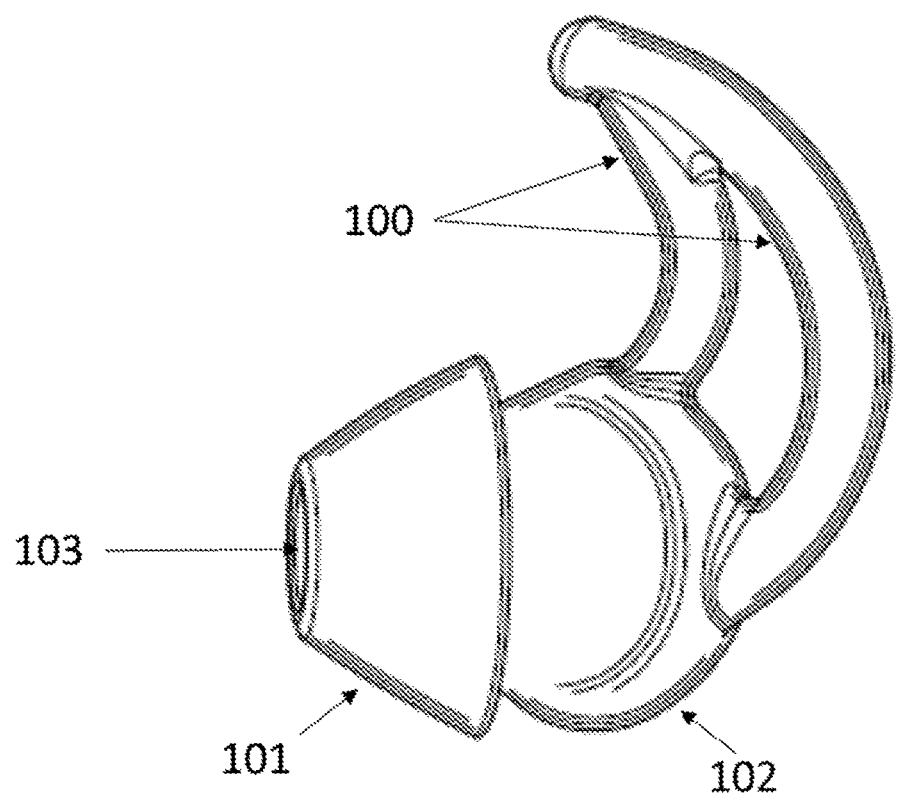
FIG. 1 shows an example of an earpiece.
Figure 2:
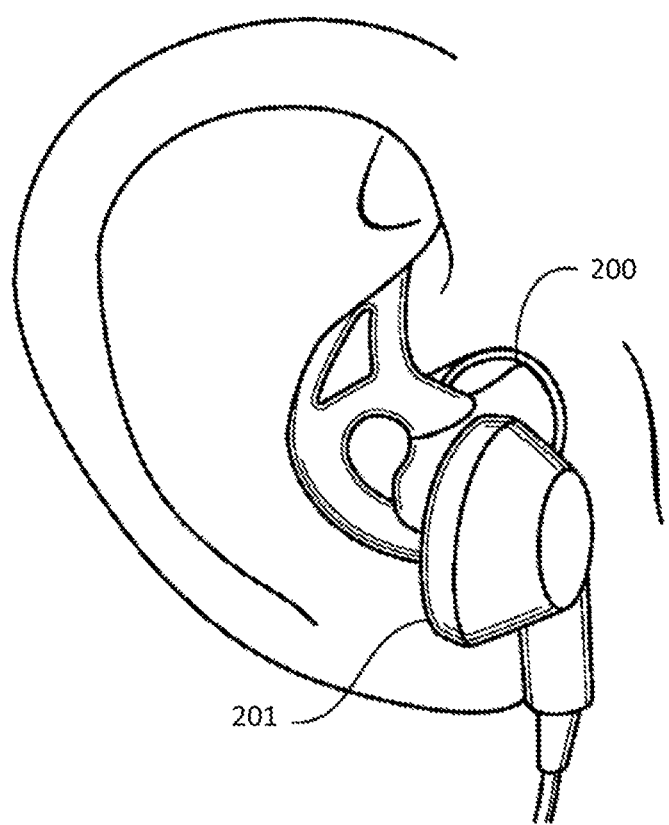
FIG. 2 shows an example of a headphone with an earpiece.

The present disclosure describes compositions that are useful for use in earpieces. The earpieces described herein are suitable for in-ear use that can be positioned in the channel of a user's ear. Typically, an earpiece includes a tip that fits into the ear canal, and a retaining structure that is configured to hold the tip in place. FIG. 1 provides an exemplary earpiece showing retaining legs 100, tip 101, body 102, and a channel 103 that allows for conducting sound waves. Being optional, in some implementations the legs are absent from the earpiece's design. An earpiece can be configured to be part of a headphone, which typically includes, at least, an acoustic driver module that includes components (e.g., electronic components, transducers, etc.) for producing audible sounds from an electrical signal. FIG. 2 shows an example of a headphone with an earpiece 200 and acoustic driver module 201. Some earpieces may be connected to an audio generation device wirelessly via a BLUETOOTH® transceiver installed within the earpiece. Some earpieces may serve as passive earplugs that lack any connections or acoustic features. As described herein, the left and right earpieces may mirror each other, but have the same structure and function, or a symmetric earpiece may fit either ear. The eartips descried herein can be customized to a particular user's ear geometry for a better fit.

The present disclosure provides an earpiece that have one or more of its components such as the tip, retaining legs, body, channel made, or a combination thereof, made from a composition that includes one or more viscoelastic materials. One or more components of the eartip (e.g., the tip and the channel) can be made from the viscoelastic materials described herein and the remaining components (e.g, body and retaining legs) can be made from elastomers such as silicone. In some examples, at least the tip of the earpiece is made from the viscoelastic materials described herein. In other examples, both the tip and channel are made from viscoelastic materials described herein. One or more of the components (e.g., tip, channel, body, and retaining legs) can be customized to an individual ear or selected from pre-designed shapes and sizes to better suit an individual ear.

Viscoelastic materials can have an elastic part, which stores energy, and a viscous part, which dissipates energy. Viscoelastic materials described herein can help improve attenuation of ambient noise that can interfere with the sounds coming through the headphones. Earpieces for in-ear devices like headphones and hearing protectors are commonly made from silicone rubbers that are insensitive to temperature and resistant to chemical attack, making it a good candidate to interface with the human body. However, most of the silicone rubbers are typically weakly viscoelastic and their moduli stay relatively constant with frequency, which can make them not a good material for noise reduction.

A low frequency storage modulus is associated with comfort because it allows conformation of the earpiece to ear geometry and is generally compliant enough to allow motion of the ear due to jaw and head motion. To achieve good passive noise rejection or passive noise attenuation, the mechanical excitations and/or mechanical vibration caused by acoustic excitation at a high modulus magnitude in the range of about 6 to about 8 kHz around body temperature (e.g., about 35° C. to about 37° C.) is desirable. The frequency range of about 6 to about 8 kHz is roughly the range of ear canal resonance frequencies, where it can be desirable to have higher passive attenuation. A material whose modulus increases as much as possible from low frequency to high frequency at about body temperature would provide comfort and good passive attenuation or passive noise rejection.

Described herein are earpieces having a tip, retaining legs, a body, a channel, or a combination thereof made from a composition including one or more elastomers, wherein the composition has a low frequency modulus metric ($M_{lf}$) of about 0.5 to about 1, a high frequency modulus metric ($M_{hf}$) of about 0.5 to about 1, and a $T_g$ (which is the maximum of the tan delta peak in dynamic mechanical testing) of about −25° C. to about 30° C.

The $M_{hf}$ value can be calculated using the following equation:

$$M_{hf} = (|E|_{6000\,Hz} / |E|_{6000\,Hz}^\circ)^{1/2}$$

where $|E|_{6000\,Hz}^\circ$ is a reference modulus value, intended to set a practical upper bound for improving passive attenuation, for example, to about 120 MPa. $|E|_{6000\,Hz}$ is the modulus measured at about body temperature (e.g., about 35° C. to about 37° C.). A wide frequency band in a body-temperature chamber was measured and 6000 Hz was selected as a representative frequency for the band where half-wave ear canal resonances are likely to occur on individuals with an earbud inserted. The reference modulus was chosen based on modeling that suggests further increasing the modulus above 120 MPa generally does not significantly improve passive noise rejection. The form of the equation (with a square) is derived from correlating modulus measurements with acoustic measurements across multiple materials. The $M_{hf}$ can be about 0.6 to about 1. For example, the $M_{hf}$ is about 0.7 to about 1, about 0.8 to about 1, or about 0.9 to about 1. The $M_{hf}$ can be about 0.5, about 0.6, about 0.7, about 0.8, about 0.9, or about 1. It is desirable to have a larger $M_{hf}$ value.

The $M_{lf}$ value can be calculated using the following equation:

$$M_{lf} = e^{\frac{-(E' - E'_{ref})^2}{2\sigma_{ref}^2}}.$$

The reference modulus $E_{ref}'$ is the target for the material at 10 Hz. A material with that modulus can provide the desirable comfort and acoustic seal (not too stiff for comfort, not too compliant so as to achieve a seal with the ear). Therefore, the metric seeks to give a score of 1 to any material with exactly the reference modulus. Deviation from the target modulus will increase the numerator of the exponent, therefore resulting in a lower score. The sigma reference value $\sigma_{ref}$ is an empirical parameter that controls how much a material is discounted for a given deviation from the target modulus. The form of the equation can discount inputs on either side of a central value. The values are also assumed measured at body temperature. The $M_{lf}$ can be about 0.6 to about 1. For example, the $M_{lf}$ is about 0.7 to about 1, about 0.8 to about 1, or about 0.9 to about 1. The $M_{lf}$ can be about 0.5, about 0.6, about 0.7, about 0.8, about 0.9, or about 1. It is desirable to have a larger $M_{lf}$ value.

The product of $M_{hf}$ and $M_{lf}$ (where the values of $M_{hf}$ and $M_{lf}$ are multiplied) can be about 0.5 to about 1, about 0.6 to about 1, about 0.7 to about 1, about 0.8 to about 1, or about 0.9 to about 1. The product can be about 0.5, about 0.6, about 0.7, about 0.8, about 0.9, or about 1. It is desirable to have a larger value for the product of $M_{hf}$ and $M_{lf}$.

The elastomer can be polynorbornene, polyurethane, styrenic-based thermoplastic elastomer, butyl rubber, acrylic, thermoplastic vulcanizates, nitrile rubber, etc., or a combination thereof. For example, the elastomer can be Versaflex™ VDT 4132 (PolyOne™).

In some implementations, the elastomer is polynorbornene (e.g., crosslinked polynorbornene). The polynorbornene can be resistant to degradation or significant swelling or softening due to ultraviolet light, bodily fluids, sebum, or cleaning solvents such as isopropyl alcohol. The polynorbornene can have a density of about 0.8 to about 1.2 kg/dm³, a hardness of about 10 to about 20 Shore A, and a tensile strength of about 2 to about 8 MPa. For example, the density is about 0.8, about 0.9, about 1.0, about 1.1, or about 1.2 kg/dm³. The hardness can be about 10 to about 15, about 15 to about 20, about 12 to about 18, or about 14 to about 16 Shore A. For example, the hardness can be about 10, about 11, about 12, about 13, about 14, about 15, about 16, about 17, about 18, about 19, or about 20 Shore A. In some implementations, the tensile strength is about 2 to about 6, about 2 to about 4, about 4 to about 8, about 4 to about 8 MPa. For example, the tensile strength can be about 2, about 3, about 4, about 5, about 6, about 7, or about 8 MPa. The polynorbornene can have a $T_g$ at about 0° C. to about 25° C.

The compositions provided herein can include polynorbornene, anti-oxidant, UV stabilizer, curatives, inhibitors, plasticizers, fillers, etc. Examples of plasticizers include oils. Polynorbornene typically has a $T_g$ at about 35° C. The incorporation of plasticizers can shift the $T_g$ to lower temperature values. For example, the polynorbonene is Norsorex M040922-1 (StarTech Advanced Materials GmbH).

The elastomer can be polyurethane. The polyurethane can be resistant to degradation or significant swelling or softening to due ultraviolet light, bodily fluids, sebum, or cleaning solvents such as isopropyl alcohol.

The compositions described herein can have a $T_g$ at about −25 to about 30, about −20 to about 30, about −15 to about 30, about −10 to about 30, about 0 to about 30° C. The $T_g$ can be about 5 to about 30° C. For example, the $T_g$ is about 5 to about 10, about 10 to about 15, about 15 to about 20, about 20 to about 25, and about 25 to about 30° C. The $T_g$ can be about 5 to about 25, about 10 to about 25, about 15 to about 25, about 20 to about 30, about 22 to about 28, or about 24 to about 26° C. For example, the $T_g$ is about 25° C.

Described herein are earpieces having a tip, retaining legs, a body, a channel, or a combination thereof made from a composition including polynorbornene, where the composition has a $M_{lf}$ of about 0.7 to about 1, a $M_{hf}$ of about 0.7 to about 1, and a $T_g$ at about 10° C. to about 30° C.

Earpieces described herein can have a tip, retaining legs, a body, a channel, or a combination thereof made from a composition which includes one or more elastomers, wherein the composition has a storage modulus of about 0.5 to about 50 MPa at about 25° C. and about 1 Hz, a glassy modulus of greater than about 400 MPa, and a $T_g$ at about −25° C. to about 30° C. In some implementations, the storage modulus can be about 1 to about 50 or about 10 to about 40 MPa. The glassy modulus can be greater than about 500, greater than about 600, greater than about 700, greater than about 800, greater than about 900, or greater than about 1000 MPa. The $T_g$ can be about 5 to about 30, about 20 to about 30, or about 5 to about 25° C. The elastomer is polynorbornene and the polynorbornene has a density of about 0.8 to about 1.2 kg/dm³, a hardness of about 10 to about 20 Shore A, and a tensile strength of about 2 to about 8 MPa. The composition can include polynorbornene, antioxidant, UV stabilizer, curatives, inhibitors, plasticizers, fillers, etc.

As used herein, and unless otherwise specified, the term "about," when used in connection with a numeric value or range of values is to indicate that the value or range of values may deviate to an extent deemed reasonable to one of ordinary skill in the art. It is well known instrument variation and other factors can affect the numerical values. The term "about" is to accommodate these variations.

What is claimed is:

1. An earpiece, wherein the earpiece:
   has a tip, retaining legs, a body, a channel, or a combination thereof made from a composition comprising one or more elastomers,
   wherein the composition has a calculated low frequency modulus metric ($M_{lf}$) score of 0.5 to 1, a calculated high frequency modulus metric ($M_{hf}$) score of 0.5 to 1, and a glass transition temperature ($T_g$) of −25° C. to 30° C.,
   wherein at least one of the one or more elastomers is polynorbornene, polyurethane, styrenic-based thermoplastic elastomer, butyl rubber, acrylic, thermoplastic vulcanizates, or nitrile rubber; and
   wherein the composition comprises anti-oxidant, UV stabilizer, curatives, inhibitors, plasticizers, or fillers.

2. The earpiece of claim 1, wherein at least one of the one or more elastomers is polynorbornene.

3. The earpiece of claim 2, wherein the polynorbornene has a density of 0.8 to 1.2 kg/dm³, a hardness of 10 to 20 Shore A, and a tensile strength of 2 to 8 MPa.

4. The earpiece of claim 1, wherein the $T_g$ is 5° C. to 30° C.

5. The earpiece of claim 1, wherein the $T_g$ is 20° C. to 30° C.

6. The earpiece of claim 1, wherein the $T_g$ is 5° C. to 25° C.

7. The earpiece of claim 1, wherein the $M_{hf}$ is 0.7 to 1.

8. The earpiece of claim 1, wherein the $M_{lf}$ is 0.7 to 1.

9. The earpiece of claim 1, wherein the product of $M_{hf}$ and $M_{lf}$ is 0.5 to 1.

10. An earpiece, wherein the earpiece:
    has a tip, retaining legs, a body, a channel, or a combination thereof made from a composition comprising polynorbornene, wherein the composition has a calculated low frequency modulus metric ($M_{lf}$) score of 0.7 to 1, a calculated high frequency modulus metric ($M_{hf}$) score of 0.7 to 1, and a $T_g$ at 10° C. to 30° C., and
    wherein the composition comprises anti-oxidant, UV stabilizer, curatives, inhibitors, plasticizers, or fillers.

11. An earpiece, wherein the earpiece:
    has a tip, retaining legs, a body, a channel, or a combination thereof made from a composition comprising one or more elastomers,
    wherein the composition has a storage modulus of 0.5 to 50 MPa at 25° C. and 1 Hz, a glassy modulus of greater than 400 MPa, and a $T_g$ at −25° C. to 30° C.,
    wherein at least one of the one or more elastomers is polynorbornene, polyurethane, styrenic-based thermoplastic elastomer, butyl rubber, acrylic, thermoplastic vulcanizates, or nitrile rubber; and
    wherein the composition comprises anti-oxidant, UV stabilizer, curatives, inhibitors, plasticizers, or fillers.

12. The earpiece of claim 11, wherein at least one of the one or more elastomers is polynorbornene and the polynorbornene has a density of 0.8 to 1.2 kg/dm³, a hardness of 10 to 20 Shore A, and a tensile strength of 2 to 8 MPa.

13. The earpiece of claim 11, wherein the composition comprises polynorbornene.

14. The earpiece of claim 11, wherein the $T_g$ is 5° C. to 30° C.

15. The earpiece of claim 11, wherein the $T_g$ is 20° C. to 30° C.

16. The earpiece of claim 11, wherein the $T_g$ is 5° C. to 25° C.

17. An earpiece, wherein the earpiece:
    has a tip, retaining legs, a body, a channel, or a combination thereof made from a composition comprising polynorbornene, wherein the composition has a calculated low frequency modulus metric ($M_{lf}$) score of 0.5 to 1, a calculated high frequency modulus metric ($M_{hf}$) score of 0.5 to 1, and a glass transition temperature ($T_g$) of −25° C. to 30° C.,
    wherein the polynorbornene has a density of 0.8 to 1.2 kg/dm³, a hardness of 10 to 20 Shore A, and a tensile strength of 2 to 8 MPa, and
    wherein the composition comprises anti-oxidant, UV stabilizer, curatives, inhibitors, plasticizers, or fillers.

* * * * *